United States Patent [19]

Effland et al.

[11] Patent Number: 4,994,472
[45] Date of Patent: Feb. 19, 1991

[54] 1-(PYRIDINYLAMINO)-2-PYRROLIDI-NONES AS PAIN RELIEVERS

[75] Inventors: Richard C. Effland, Bridgewater; David G. Wettlaufer, Phillipsburg, both of N.J.

[73] Assignee: Hoechst-Roussel Pharmaceuticals Incorporated, Somerville, N.J.

[21] Appl. No.: 388,413

[22] Filed: Aug. 2, 1989

[51] Int. Cl.$^5$ .................. A61K 31/44; C07D 401/00; C07D 211/00
[52] U.S. Cl. .................. 514/333; 546/256; 546/281; 546/15; 514/343
[58] Field of Search .................. 546/256, 281, 15; 514/333, 343, 342

[56] References Cited

U.S. PATENT DOCUMENTS 4,324,884  4/1982  White et al. .................. 546/256
4,752,610  6/1988  Effland .................. 546/256

OTHER PUBLICATIONS

Blokhina et al., Khim. Geterotsikl. Soedin., 4, 474–478 (1987).
Baldwin et al., Tetrahedron, vol. 42, No. 15, pp. 4247–4252, (1986).
Baldwin et al., J. Chem. Soc., Chem. Commun., (16), 1095–1096, (1984).

Primary Examiner—Mary C. Lee
Assistant Examiner—Robert C. Whittenbaugh
Attorney, Agent, or Firm—Elliott Korsen

[57] ABSTRACT

This invention relates to 1-(pyridinylamino)-2-pyrrolidinones of the formula

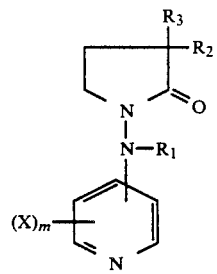

wherein $R_1$, $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl or $R_2$ and $R_3$ together form a cycloalkane ring of 4 to 6 carbons or a spiro-fused aryl or heteroaryl substituted cycloalkane; X is hydrogen, halogen, hydroxy, loweralkyl, loweralkoxy, nitro, amino or trifluoromethyl; m is an integer of 1 to 3, the pharmaceutically acceptable acid addition salts thereof and where appropriate the geometrical, optical and stereoisomers and racemic mixtures thereof. The compounds of this invention display utility as analgesics, for enhancing memory and for the treatment of Alzheimer's disease.

23 Claims, No Drawings

1-(PYRIDINYLAMINO)-2-PYRROLIDINONES AS PAIN RELIEVERS

This invention relates to compounds of the formula

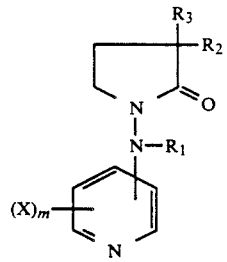
(I)

wherein $R_1$, $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl or $R_2$ and $R_3$ together form a cycloalkane ring of 4 to 6 carbons or a spiro-fused aryl or heteroaryl substituted cycloalkane; X is hydrogen, halogen, hydroxy, loweralkyl, loweralkoxy, nitro, amino or trifluoromethyl; m is an integer of 1 to 3, the pharmaceutically acceptable acid addition salts thereof and where appropriate the geometrical, optical and stereoisomers and racemic mixtures thereof. The compounds of this invention display utility as analgesics, for enhancing memory and for the treatment of Alzheimer's disease.

Preferred embodiments of the invention are those of Compound I where $R_1$ is selected from hydrogen and loweralkyl; $R_2$ is selected from hydrogen, loweralkyl, and arylloweralkyl; $R_3$ is selected from hydrogen, loweralkyl, and arylloweralkyl.

Most preferred embodiments of the invention are those of Compound I where $R_1$ is selected from hydrogen and loweralkyl; $R_2$ is selected from hydrogen and loweralkyl; and $R_3$ is selected from hydrogen and loweralkyl.

Throughout the specification and the appended claims, a given chemical formula or name shall encompass all optical and stereoisomers thereof where such isomers and mixtures exist.

In the above definition, the term "lower" means the group it is describing contains from 1 to 6 carbon atoms. The term "alkyl" refers to a straight or branched chain hydrocarbon containing no unsaturation, e.g., methyl, ethyl, isopropyl, t-butyl, neopentyl, n-hexyl, etc.; the term "arylloweralkyl" refers to a monovalent substituent which consists of an "aryl" group e.g., phenyl, o-tolyl, m-methoxyphenyl, etc., as defined by the formula

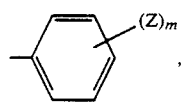

where Z is as defined below, and m is an integer of 1 to 3, linked through a loweralkylene group having its free valance bond from a carbon of the loweralkylene group, and having a formula of—loweralkylene

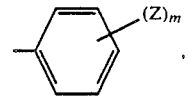

where Z is hydrogen, halogen, hydroxy, loweralkyl, loweralkoxy, $CF_3$, $NO_2$, $NH_2$ and where m is as previously defined; the term "alkylene" refers to a bivalent radical of the lower branched or unbranched alkyl group it is derived from having valence bonds from two terminal carbons thereof; e.g., methylene (—$CH_2$—), ethylene (—$CH_2CH_2$—), propylene (—$CH_2CH_2CH_2$—), isopropylene $$(CH_3\overset{|}{C}H-CH_2-),$$

etc,; the term "heteroaryl" refers to an aromatic heterocyclic mono- or bicyclic radical, e.g., pyridyl, thiophene, etc.; and the term "heteroarylloweralkyl" refers to a loweralkyl group having a heteroaryl substituent thereon; the term "alkoxy" refers to a monovalent substituent which consists of an alkyl group linked through an ether oxygen having its free valence bond from ether oxygen, e.g., methoxy, ethoxy, propoxy, butoxy, pentoxy, etc.; and the term "halogen" refers to a member of the halogen family consisting of fluorine, chlorine, bromine and iodine.

The compounds of the present invention are prepared in the following manner. The substituents are as defined above unless indicated otherwise.

An aminopyrrolidinone of the formula

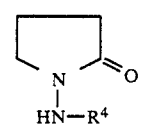
(II)

where $R^4$ is hydrogen or loweralkyl is reacted with a halopyridine hydrochloride of the formula

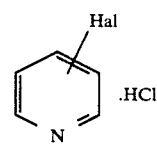

where Hal is a halogen, to afford Compound I of the invention of the formula

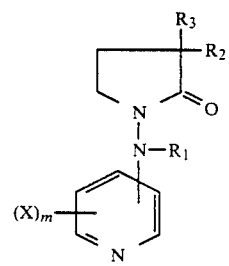
(I)

This reaction typically takes place in a loweralkanol or phenolic solvent, e.g., phenol, isopropanol, etc., in an inert atmosphere, e.g., nitrogen, at a temperature of 90° to 150° C. for ½ to 18 hours.

Compound II is well known or can be synthesized by conventional techniques well known in the art. For example, Compound II can be prepared following the teachings of G. Pagliarini in CA 65:7125a.

Compounds of the present invention are useful as analgesic agents due to their ability to alleviate pain in mammals. The activity of the compounds is demonstrated in the phenyl-para-quinone writhing assay in mice, a standard assay for analgesia [Proc. Soc. Exptl. Biol. Med., 95, 729 (1957)]. Presented in Table I is the analgesic effect of one of the compounds of the invention expressed as the % decrease in writhing at a given dose. The standard is expressed as the subcutaneous dose at which 50% of the phenyl-para-quinone induced writhing is inhibited in the animals, i.e., the $ED_{50}$ value.

TABLE I

| Compound | % Inhibition of Writhing |
| --- | --- |
| 1-(4-pyridinylamino)-2-pyrrolidinone | −56% at 20 mg/kg s.c. |
| Aspirin (standard) | $ED_{50}$ = 32.8 mg/kg s.c. |

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are examples only and that they do not, to any extent, limit the scope or practice of the invention.

The compounds of the present invention are also useful in the treatment of various memory dysfunctions characterized by decreased cholinergic function such as Alzheimer's Disease.

This utility is demonstrated in the Dark Avoidance Assay.

DARK AVOIDANCE ASSAY

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chambers, the animal re-enters the dark compartment shortly after being placed in the test chamber 24 hours later. The effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. The activity in the assay of some of the compounds of the invention are given below in Table 2.

TABLE 2

| Compound | Dose (mg/kg of body wt) | % of Animals With Scopolamine Induced Memory Deficit Reversal |
| --- | --- | --- |
| 1-(Propyl-4-pyridinyl-amino)-2-pyrrolidinone oxalate | .3 mg/kg s.c. | 33% |
| Tacrine (standard) | .63 s.c. | 13% |
| Pilocarpine (standard) | 1.25 s.c. | 19% |

Effective amounts of the present invention may be administered to subject by any one of various methods, for example, orally as in capsules or tablets, parenterally in the form of sterile solutions or suspensions, and in some cases intravenously in the form of sterile solution. The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ®, corn starch and the like; a lubricant such as magnesium strearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
1-(Ethyl-4-pyridinylamino)-3-methyl-2-pyrrolidinone;
1-[(3-Nitro-4-pyridinyl)amino]-2-pyrrolidinone;
1-[(3-Methyl-4-pyridinyl)propylamino]-2-pyrrolidinone;
1-[(3-Amino-4-pyridinyl)butylamino]-3,3-dimethyl-2-pyrrolidinone;
3-Ethyl-1-[(3-ethyl-4-pyridinyl)methylamino]-2-pyrrolidinone;
1-(Ethyl-4-pyridinylamino)-3-phenylmethyl-2-pyrrolidinone;
1-[(3-Fluoro-4-pyridinyl)propylamino]-3,3-dimethyl-2-pyrrolidinone;
3-Propyl-1-[propyl-(3-propyl-4-pyridinyl)amino]-2-pyrrolidinone;
1-8 Butyl-(3-nitro-4-pyridinyl)amino]-3,3-diethyl-2-pyrrolidinone;
1-[Methyl-(3-methyl-4-pyridinyl)amino]-3-(2-phenylethyl)-2-pyrrolidinone;
1-(Ethyl-4-pyridinylamino)-3-propyl-2-pyrrolidinone;
1-[Propyl-[3-(trifluoromethyl)-4-pyridinyl]amino]-2-pyrrolidinone;
1-[(3-Amino-4-pyridinyl)butylamino]-3,3-dipropyl-2-pyrrolidinone;
1-(Propyl-3-pyridinylamino)-2-pyrrolidinone;
1-[(4-Methyl-3-pyridinyl)propylamino]-2-pyrrolidinone;
1-[(4-Fluoro-3-pyridinyl)propylamino]-3,3-dimethyl-2-pyrrolidinone;
1,3-Dihydro-1'-(4-pyridinylamino)spiro[2H-indene-2,3'-[3H]]-2'-pyrrolidinone.

The following examples are for illustrative purposes only and are not to be construed as limiting the invention. All temperatures are given in degrees centigrade (°C.) unless otherwise designated.

EXAMPLE 1

1-(4-Pyridinylamino)-2-pyrrolidinone

A slurry consisting of 1-amino-2-pyrrolidinone (7.40 g), phenol (17.8 g), and 4-bromopyridine hydrochloride (15.8 g) was heated in a 140° C. oil bath for 70 minutes under nitrogen. The resulting solution was cooled to room temperature and purified via flash column chromatography (silica gel, 2% Et$_3$N/0–50% MeOH/EtOAc) and preparative high performance liquid chromatography (HPLC) (silica gel, 10% MeOH/DCM). The resulting product fractions were concentrated and the product was redissolved in dichloromethane and sat. aqueous sodium bicarbonate. Exhaustive extraction of the aqueous layer afforded the pure product (free of triethyl amine salts). Recrystallization from dichloromethane/ether afforded 2.10 g (16%) of 1-(4-pyridinylamino)-2-pyrrolidinone, m.p. 177°–179.5° C.

Analysis. Calculated for C$_9$H$_{11}$N$_3$O: 61.00% C; 6.26% H; 23.71% N. Found: 60.94% C; 6.27% H; 23.76% N.

EXAMPLE 2

1-(Propyl-4-pyridinylamino)-2-pyrrolidinone oxalate

A slurry consisting of 1-(propylamino)-2-pyrrolidinone (7.96 g), 4-chloropyridine hydrochloride (6.31 g) and phenol (20.9 g) was heated in a 143° C. oil bath under nitrogen. After 30 min., the resulting solution was treated with additional 4-chloropyridine hydrochloride (6.30 g) and heated for an additional 30 minutes. The mixture was cooled to room temperature and diluted with dichloromethane. The organic layer was washed with dilute aqueous sodium bicarbonate and the combined aqueous layers back-extracted with dichloromethane and ether. The combined organic layers were washed with brine and dried (K$_2$CO$_3$). Filtration, concentration, and purification via flash column chromatography (silica gel, 10% MeOH/DCM) and preparative HPLC afforded 3.65 g (30%) of 1-(propyl-4-pyridinylamino)-2-pyrrolidinone as an oil. The oxalate was prepared with 1.0 eq. oxalic acid in absolute ethanol, m.p. 194°–195.5° C.

Analysis. Calculated for C$_{14}$H$_{19}$N$_3$O$_5$: 54.36% C; 6.19% H; 13.58% N. Found: 54.39% C; 6.18% H; 13.55% N.

We claim:

1. A 1-(pyridinylamino)-2-pyrrolidinone of the formula

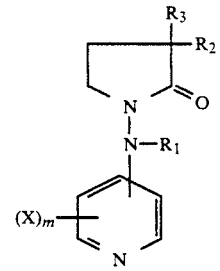

wherein R$_1$, R$_2$ and R$_3$ are independently hydrogen, loweralkyl, aryl, arylloweralkyl or heteroarylloweralkyl selected from the group consisting of pyridinylmethyl, pyridinylethyl, thienylmethyl, thienylethyl or R$_2$ and R$_3$ together form a cycloalkane ring of 4 to 6 carbons or a spiro-fused aryl or heteroaryl substituted cycloalkane; the term "heteroaryl" signifying an aromatic heterocyclic radical selected from pyridyl or thiophene; X is hydrogen, halogen, hydroxy, loweralkyl, loweralkoxy, nitro, amino or trifluoromethyl; m is an integer of 1 to 3, or the pharmaceutically acceptable acid addition salts thereof and where appropriate the geometrical, optical and stereoisomers and racemic mixtures thereof.

2. A compound as defined in claim 1 wherein $R_1$ is hydrogen or loweralkyl, $R_2$ is hydrogen, loweralkyl or arylloweralkyl and $R_3$ is hydrogen, loweralkyl or arylloweralkyl.

3. A compound as defined in claim 2 wherein $R_1$ is hydrogen or loweralkyl, $R_2$ is hydrogen or loweralkyl and $R_3$ is hydrogen or loweralkyl.

4. A compound as defined in claim 3 wherein $R_1$ is loweralkyl.

5. The compound as defined in claim 4 which is 1-(propyl-4-pyridinylamino)-2-pyrrolidinone.

6. A compound as defined in claim 3 wherein $R_1$ is hydrogen.

7. The compound as defined in claim 1 which is 1-(4-pyridinylamino)-2-pyrrolidinone.

8. An analgesic composition which comprises an effective pain alleviating amount of a compound as defined in claim 1.

9. A composition as defined in claim 8 wherein $R_1$ is hydrogen or loweralkyl, $R_2$ is hydrogen, loweralkyl or arylloweralkyl and $R_3$ is hydrogen, loweralkyl or arylloweralkyl.

10. A composition as defined in claim 9 wherein $R_1$ is hydrogen or loweralkyl, $R_2$ is hydrogen or loweralkyl and $R_3$ is hydrogen or loweralkyl.

11. A composition as defined in claim 10 wherein $R_1$ is loweralkyl.

12. The composition as defined in claim 11 which comprises 1-(propyl-4-pyridinylamino)-2-pyrrolidinone.

13. A compound as defined in claim 10 wherein $R_1$ is hydrogen.

14. The composition as defined in claim 13 which comprises 1-(4-pyridinylamino)-2-pyrrolidinone.

15. A pharmaceutical composition which comprises an effective memory enhancing amount of a compound as defined in claim 1.

16. A composition as defined in claim 15 wherein $R_1$ is hydrogen or loweralkyl; $R_2$ is hydrogen, loweralkyl or arylloweralkyl and $R_3$ is hydrogen, loweralkyl or arylloweralkyl.

17. A composition as defined in claim 16 wherein $R_1$, $R_2$ and $R_3$ are independently selected from hydrogen or loweralkyl.

18. A composition as defined in claim 17 wherein $R_1$ is loweralkyl.

19. The composition as defined in claim 18 which comprises 1-(propyl-4-pyridinylamino)-2-pyrrolidinone.

20. A composition as defined in claim 17 wherein $R_1$ is hydrogen.

21. The composition as defined in claim 20 which comprises 1-(4-pyridinylamino)-2-pyrrolidinone.

22. A method of alleviating pain in a mammal which comprises administering to a mammal a pain alleviating effective amount of a compound as defined in claim 1.

23. A method of treating a mammal in need of memory enhancement which comprises administering to a mammal a memory enhancing effective amount of a compound as defined in claim 1.

* * * * *